(12) United States Patent
Lewis

(10) Patent No.: US 6,565,575 B2
(45) Date of Patent: May 20, 2003

(54) METHOD AND APPARATUS FOR REMOVING AN ACETABULAR CUP

(76) Inventor: Randall J. Lewis, 2021 K. St. NW., Washington, DC (US) 20006

( * ) Notice: Subject to any disclaimer, the term of this patent is extended or adjusted under 35 U.S.C. 154(b) by 0 days.

(21) Appl. No.: 09/953,827

(22) Filed: Sep. 17, 2001

(65) Prior Publication Data

US 2002/0116007 A1 Aug. 22, 2002

Related U.S. Application Data

(60) Provisional application No. 60/269,615, filed on Feb. 16, 2001.

(51) Int. Cl.$^7$ .............................................. A61B 17/58
(52) U.S. Cl. ...................................................... 606/99
(58) Field of Search ............................... 606/81, 91, 99, 606/86, 82; 623/22.21

(56) References Cited

U.S. PATENT DOCUMENTS

| | | | | |
|---|---|---|---|---|
| 5,830,215 A | * | 11/1998 | Incavo et al. .................. | 606/79 |
| 5,919,195 A | * | 7/1999 | Wilson et al. ................. | 606/80 |
| 6,022,357 A | * | 2/2000 | Reu et al. ....................... | 606/99 |
| 6,059,833 A | * | 5/2000 | Doets ........................ | 623/22.21 |
| 6,063,123 A | * | 5/2000 | Burrows et al. .......... | 623/22.21 |
| 6,063,124 A | * | 5/2000 | Amstutz .................... | 623/22.21 |
| 6,152,930 A | * | 11/2000 | Mastrorio ..................... | 606/99 |
| 6,395,005 B1 | * | 5/2002 | Lovell ........................... | 606/91 |

* cited by examiner

*Primary Examiner*—Eduardo C. Robert
(74) *Attorney, Agent, or Firm*—Baker & Daniels

(57) ABSTRACT

The present invention provides an improved method and apparatus for removing an acetabular cup from an acetabulum. An osteotome instrument includes an elongated handle shaft terminating in a head portion. One of a plurality of interchangeable spherical heads, and one of a plurality of interchangeable osteotomes having curved blades, may be attached to the head portion of the instrument, and are selected based upon the size of the acetabular cup to be removed. In use, the spherical head of the instrument is seated within the recess of the liner of the acetabular cup such that the end of the osteotome blade is disposed closely adjacent the rim of the acetabular cup. Thereafter, the handle shaft of the instrument may be pivoted and/or rotated to make several cuts with the curved osteotome blade, which are closely adjacent the outer hemispherical surface of the acetabular cup, until the acetabular cup may be removed from the acetabulum.

18 Claims, 4 Drawing Sheets

FIG._1

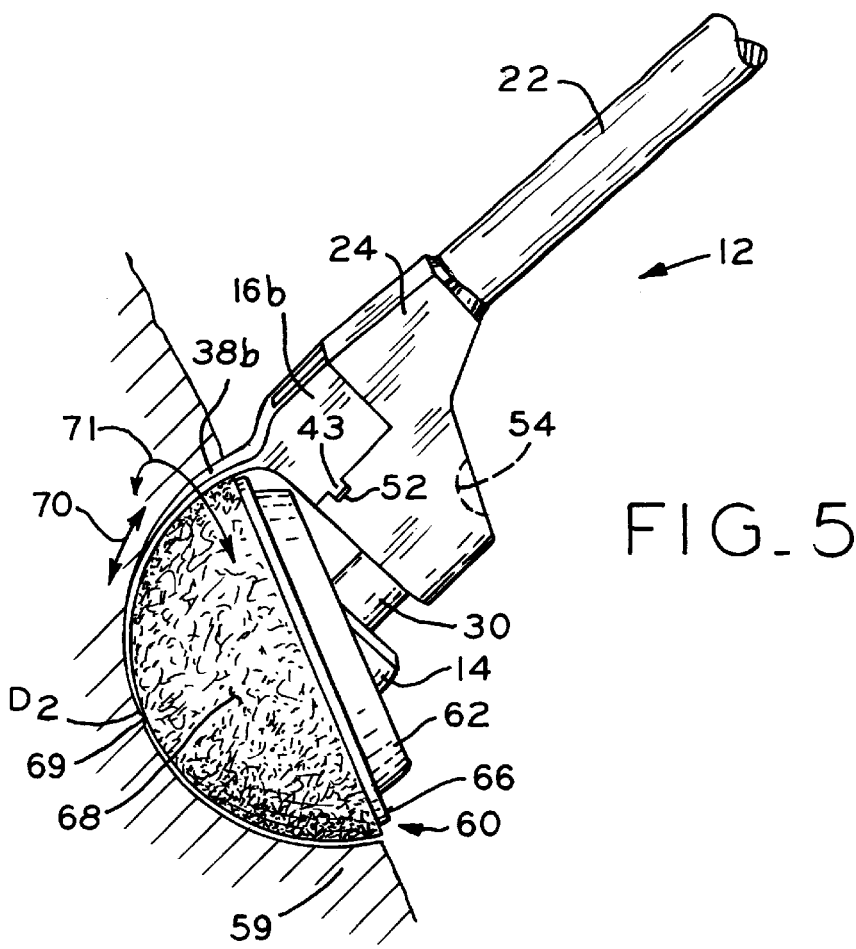
FIG_5
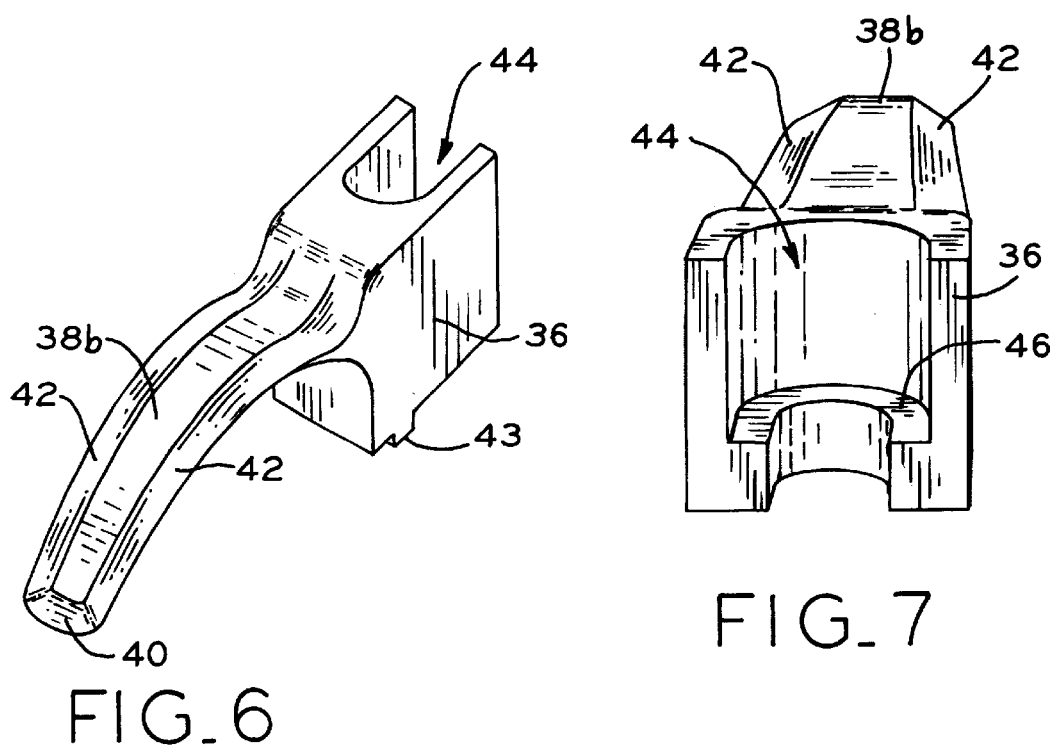
FIG_6
FIG_7

METHOD AND APPARATUS FOR REMOVING AN ACETABULAR CUP

CROSS REFERENCE TO RELATED APPLICATIONS

This application claims the benefit under Title 35, U.S.C. §119(e) of U.S. Provisional Patent Application Ser. No. 60/269,615, entitled METHOD AND APPARATUS FOR REMOVING AN ACETABULAR CUP, filed on Feb. 16, 2001.

BACKGROUND OF THE INVENTION

1. Field of the Invention

The present invention relates to ball-and-socket prosthetic hip joints, which include an acetabular cup positioned within a patient's acetabulum to serve as the socket for the hip joint, and more particularly, to a method and apparatus for removing the acetabular cup from the acetabulum.

2. Description of the Related Art

Prosthetic ball-and-socket hip joints generally include a femoral component and an acetabular component, the acetabular component including an acetabular cup positioned in a patient's acetabulum which serves as the "socket" for the hip joint. The acetabular cup is typically made of stainless steel or titanium, having a hemispherical outer surface which can be roughened to allow the acetabular bone to grow therein to anchor the acetabular cup within the acetabulum. Additionally, a liner of suitable material, such as ultra-high molecular weight polyethylene (UHMWPE) for example, is received within the acetabular cup, and includes a hemispherical recess for receiving the ball end of the femoral component of the prosthetic hip joint.

During a prosthetic hip joint revision procedure, the acetabular cup is removed from the acetabulum and replaced with a new acetabular cup. To remove the acetabular cup, a chisel-like osteotome is used, which includes a blade for cutting through the acetabular bone surrounding the hemispherical outer surface of the acetabular cup, and a head which may be struck by a mallet to drive the blade through the bone adjacent the acetabulum. In use, the blade of the osteotome is positioned near the acetabular cup, and the head of the osteotome is struck with the mallet to make a cut in the bone adjacent the acetabular cavity near the acetabular cup. Thereafter, the osteotome is withdrawn and repositioned, and the procedure is repeated until sufficient cuts have been made around the acetabular cup to permit removal thereof from the acetabulum. Thereafter, a new acetabular cup is positioned within the acetabulum.

What is needed is an improved apparatus and method for quickly and easily removing an acetabular cup from an acetabulum with minimal loss of acetabular bone, while preserving a relatively intact, hemispherical acetabular recess into which a new acetabular cup may be fitted.

SUMMARY OF THE INVENTION

The present invention provides an improved method and apparatus for removing an acetabular cup from an acetabulum. A surgical kit includes an osteotome instrument having an elongated handle shaft terminating in a head portion, and a plurality of interchangeable osteotomes and pivot elements, such as spherical heads, which may be attached to the head portion of the instrument. Each spherical head is sized to be received within the recess of an acetabular cup liner of a corresponding size, and at least two osteotomes, having curved blades of different lengths, are sized for use with acetabular cups of different sizes. When a corresponding spherical head and osteotome are attached to the instrument, the spacing between the osteotome blade and center of the spherical head corresponds to the spacing between the center of the recess in the acetabular cup liner and the rim of the acetabular cup. The blade of each osteotome is curved to generally match the curvature of the outer hemispherical surface of the acetabular cup.

In use, the spherical head of the instrument is seated within the recess of the acetabular cup liner such that the end of the osteotome blade is disposed closely adjacent the rim of the acetabular cup. In this manner, the position of the blade is fixed relative to the rim of the acetabular cup due to the seating of the spherical head within the recess of the acetabular cup liner and the spacing between the osteotome blade and the spherical head. Thereafter, the handle shaft of the instrument may be pivoted and/or rotated to make several cuts with the curved osteotome blade which are closely adjacent the outer hemispherical surface of the acetabular cup, until the acetabular cup may be removed from the acetabulum.

In one embodiment of the present method, a first osteotome having a short blade may be used to cut around the outer hemispherical surface of the acetabular cup to a first depth. Thereafter, the first osteotome is removed from the instrument, and a second osteotome having a longer blade is attached thereto. The second osteotome is then used to cut around the outer hemispherical surface of the acetabular cup to the apex thereof, after which the acetabular cup may be removed.

Each osteotome blade may include a cutting surface along the end thereof for cutting acetabular bone in an arc from the rim of the acetabular cup toward the apex thereof, as well as a pair of side cutting surfaces for cutting in an orbital manner about the acetabular cup.

The handle shaft of the instrument may include a radially projecting handle lever to facilitate rotation of the instrument, and an impaction head at a proximal end of the handle shaft which may be struck by a mallet as necessary to drive the osteotome blade.

Advantageously, the seating of the spherical head of the instrument within the recess of the acetabular cup liner centers the instrument with respect to the acetabular cup, with the osteotome blade spaced a fixed distance from the spherical head and closely adjacent the outer hemispherical surface of the acetabular cup. Thus, the osteotome blade is guided during cutting by the spherical head to cut closely adjacent the acetabular cup such that loss of acetabular bone is minimized, and an intact, hemispherically-shaped acetabular recess remains after removal of the acetabular cup into which a new acetabular cup may be fitted.

Additionally, removal of an acetabular cup using the present instrument and method requires much less time than acetabular cup removal using prior osteotomes, thereby shortening the length of a prosthetic hip joint revision procedure.

In one form thereof, the present invention provides an apparatus for removing an acetabular cup from an acetabulum, the apparatus including a handle; a pivot element connected to the handle, the pivot element dimensioned to be received within an acetabular cup; and a blade connected to the handle and spaced from the pivot element, such that when the pivot element is received within the acetabluar cup, the blade is disposed externally of the acetabular cup closely adjacent an outer surface of the acetabular cup.

In another form thereof, the present invention provides a kit for removing an acetabular cup from an acetabulum, including an osteotome instrument; a spherical head removably mountable to the instrument, the spherical head sized to be received within an acetabular cup; and a blade removably mountable to the instrument.

In another form thereof, the present invention provides a method for removing an acetabular cup from an acetabulum, the acetabular cup having an outer surface, the method including the steps of providing an instrument including a spherical head and a blade, the spherical head and the blade spaced from one another; seating the spherical head within the acetabular cup; moving the instrument to make a series of cuts with the blade which are closely adjacent the outer surface of the acetabular cup; and removing the acetabular cup from the acetabulum.

BRIEF DESCRIPTION OF THE DRAWINGS

The above-mentioned and other features and advantages of this invention, and the manner of attaining them, will become more apparent and the invention itself will be better understood by reference to the following description of an embodiment of the invention taken in conjunction with the accompanying drawings, wherein:

FIG. 5 is a partial sectional view showing the osteotome instrument of FIG. 3 with an osteotome having a long blade attached thereto, the osteotome blade cutting bone adjacent the acetabulum to a second depth at the apex of the acetabular cup;

FIG. 6 is a front perspective view of an interchangeable osteotome having a long blade, for use with the osteotome instrument of FIGS. 2–5; and FIG. 7 is a rear perspective view of the interchangeable osteotome of FIG. 6.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION

Figure 1:
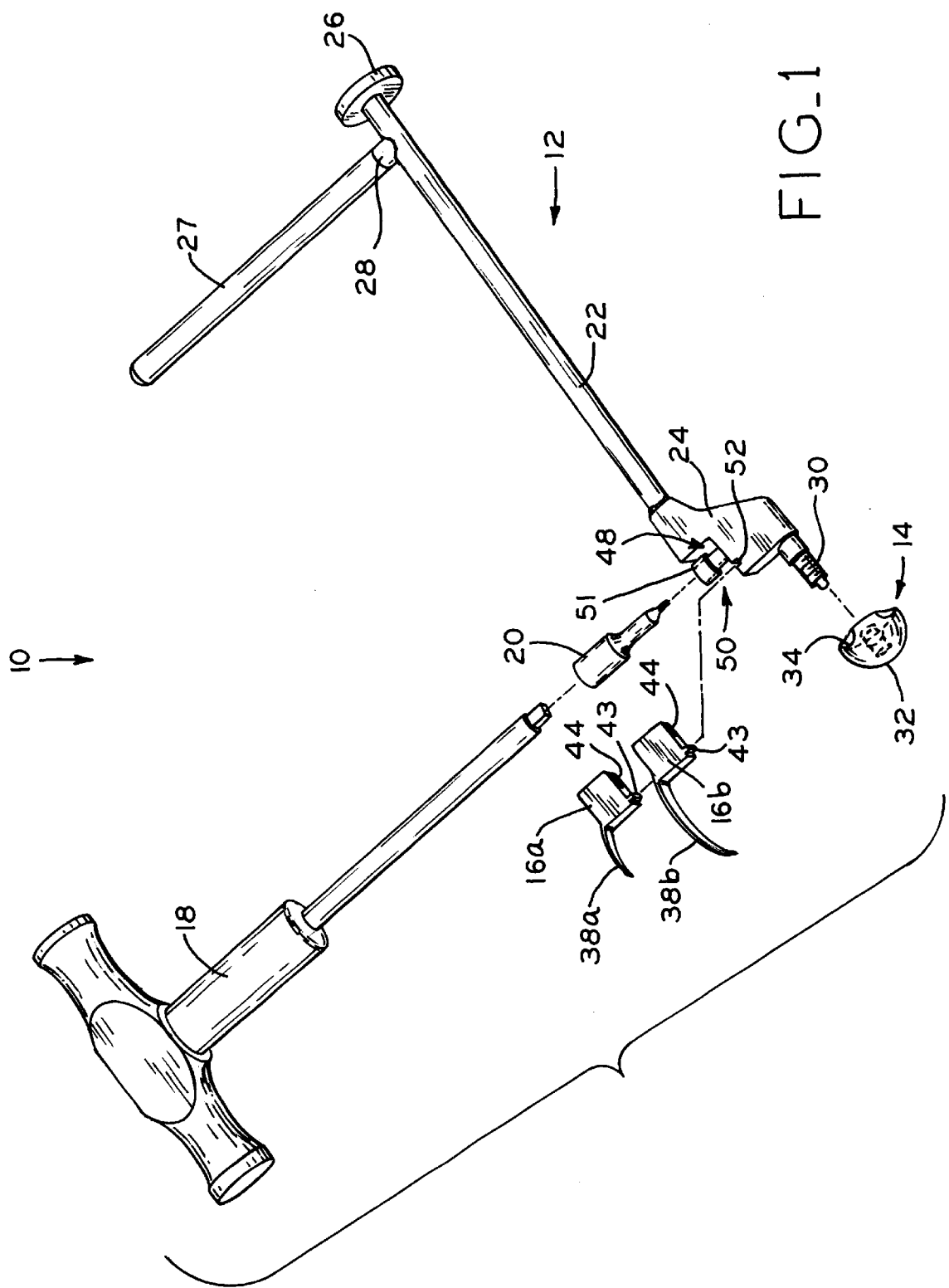
FIG. 1 is a perspective view of the components of a surgical kit in accordance with the present invention, including an osteotome instrument, an interchangeable spherical head, a pair of interchangeable blades, a torque wrench, and an adaptor.

Referring to FIG. 1, surgical kit 10 is shown, which generally includes osteotome instrument 12, one of a plurality of interchangeable pivot elements such as spherical heads 14, a plurality of interchangeable osteotomes 16a, 16b, torque wrench 18 and adaptor 20 for securing osteotomes 16a, 16b to osteotome instrument 12. Osteotome instrument 12 includes handle shaft 22 having head 24 at a distal end thereof, and impaction head 26 threaded onto a proximal end thereof. Handle lever 27 is threaded into shoulder 28 of handle shaft 22. Handle shaft 22 and handle lever 26 may be grasped to manipulate osteotome instrument 12, as described in further detail below.

Head 24 of osteotome instrument 12 includes threaded shaft 30 projecting therefrom generally parallel to handle shaft 22, onto which spherical head 14 may be threaded to attach spherical head 14 to osteotome instrument. Spherical head 14 includes a substantially spherical pivot surface 32 with a plurality of indentations 34 therein to allow spherical head 14 to be easily grasped during attachment of spherical head 14 to threaded shaft 30, or detachment therefrom. Surgical kit 10 may include a plurality of spherical heads 14 of different diameters for use with acetabular cup liners of different sizes, each spherical head 14 including one or more osteotomes 16a, 16b sized for use with acetabular cups of different sizes. Suitable spherical heads and osteotomes are selected depending upon the dimensions of the acetabular cup to be removed such that, when a corresponding spherical head and osteotome are attached to the instrument, the spacing between the osteotome blade and center of the spherical head corresponds to the spacing between the center of the recess in the acetabular cup liner and the rim of the acetabular cup.

Osteotomes 16a, 16b may be interchangeably connected to head 24 of instrument 12. Osteotome 16b is shown in FIGS. 6 and 7, and includes head portion 36 with curved blade 38b extending therefrom. Blade 38b includes end cutting surface 40 and a pair of side cutting surfaces 42. Head portion 36 of osteotome 16b also includes tooth 43, and slot 44 having semi-annular ledge 46.

Referring again to FIG. 1, osteotome instrument 12 further includes an osteotome-receiving recess 48 in head 24 thereof, having notch 52. Osteotome clamping screw 50 is disposed within recess 48 and threaded into head 24 of osteotome instrument 12. Osteotome clamping screw 50 is moveable between loosened and tightened positions, and further, may be retained by head 24 in the loosened position to prevent detachment of osteotome clamping screw 50 to simplify the interchanging of osteotomes 16a, 16b during a surgical procedure. As shown in FIG. 1, to attach an osteotome, such as osteotome 16a, for example, to instrument 12, osteotome 16a is placed within recess 48 such that osteotome clamping screw 50 is disposed within slot 44 of osteotome 16a, and tooth 43 of osteotome 16a is fitted within notch 52 of head 24, with blade clamping screw 50 in a loosened position. Thereafter, osteotome clamping screw 50 is tightened using torque wrench 18 and adaptor 20 such that head 51 of osteotome clamping screw 50 engages ledge 46 of osteotome 16a to secure osteotome 16a to instrument 12. Torque wrench 18 may be adjusted to deliver a predetermined amount of torque to osteotome clamping screw 50, to prevent head 51 of osteotome clamping screw 50 from being tightened onto ledge 46 of osteotome 16a beyond a desired clamping force.

Figure 2:
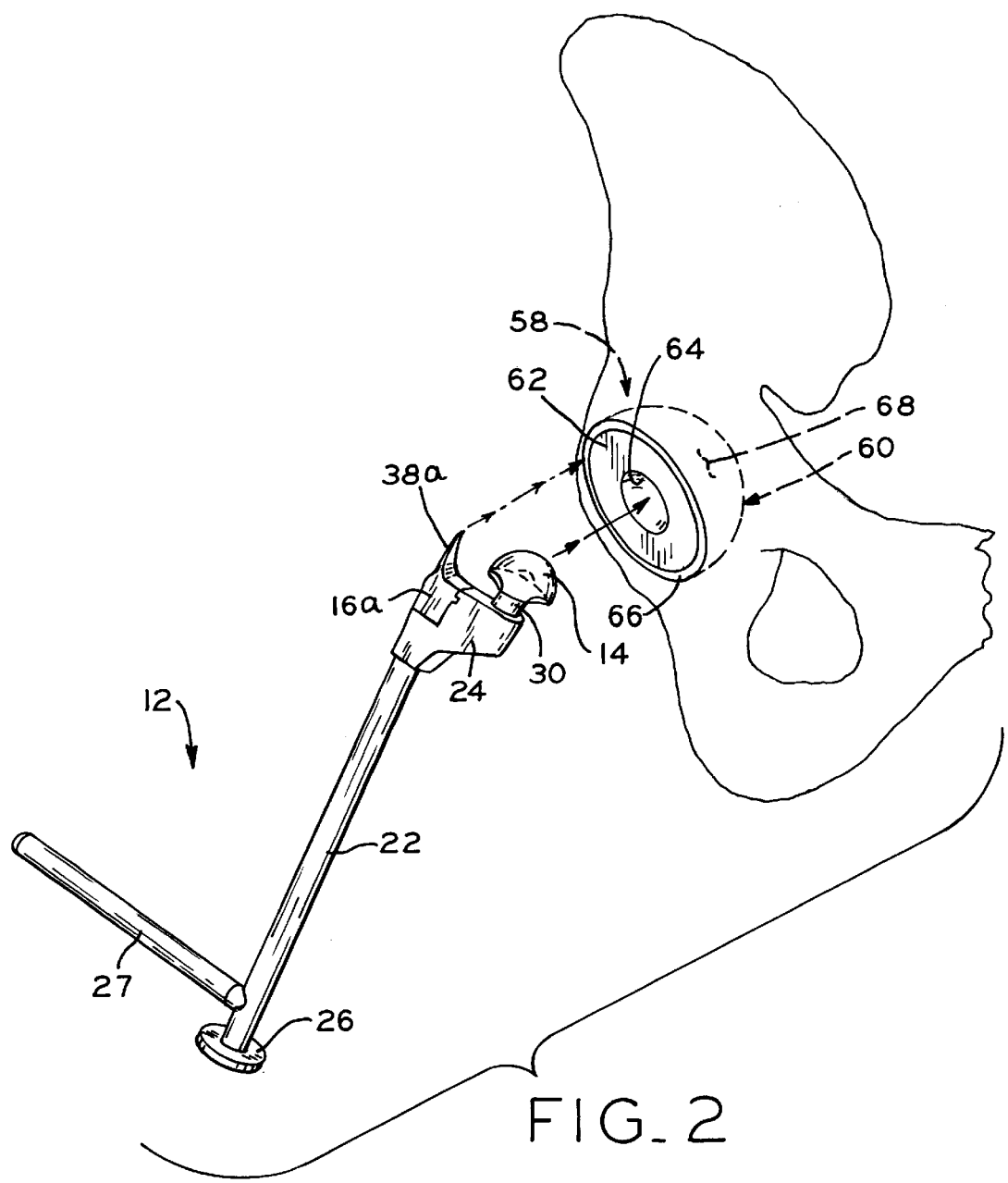
FIG. 2 is a perspective view of an acetabulum of a hip joint including an acetabular cup fitted therein, and an osteotome instrument of the present invention being operatively coupled thereto.
Figure 3:
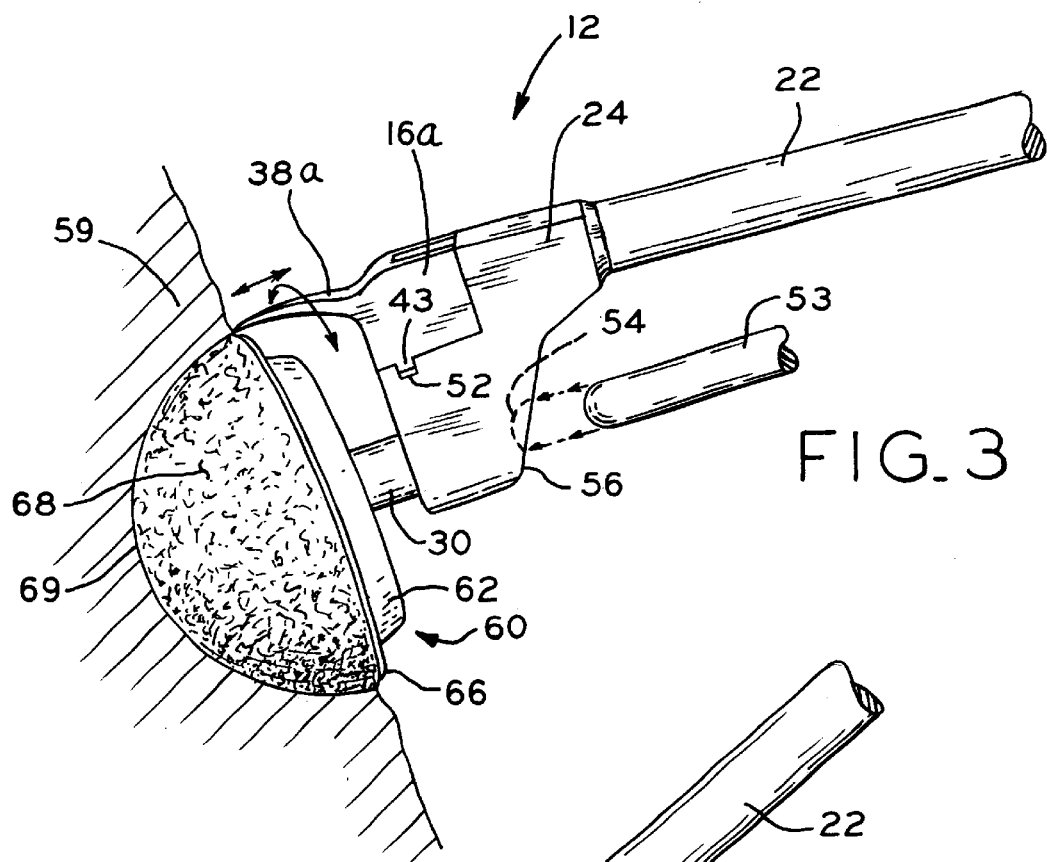
FIG. 3 is a partial sectional view through the acetabulum of FIG. 2, showing the spherical head of the osteotome instrument of FIG. 2 seated within the acetabular cup liner of the acetabular cup prior to cutting with an osteotome having a short blade.

Referring to FIGS. 2–5, the use of osteotome instrument 12 to remove an acetabular cup 60 will now be described. As shown in FIGS. 2 and 3, a first osteotome 16a having short blade 38a is attached to instrument 12 as described above. Then, spherical head 14 of osteotome instrument 12 is seated within hemispherical recess 64 of liner 62 of acetabular cup 60, which is anchored in acetabulum 58. Rod 53 may be pressed against indentation 54 in rear side 56 of head 24 to aid in seating spherical head 14 within recess 64 of acetabular cup 60. As shown in FIG. 3, blade 38a of osteotome 16a is spaced a distance from the center of spherical head 14 which corresponds to the distance between the center of recess 64, or the center of spherical head 14, and rim 66 of acetabular cup 60, such that blade 38a is disposed closely adjacent outer hemispherical surface 68 of acetabular cup 60.

Figure 4:
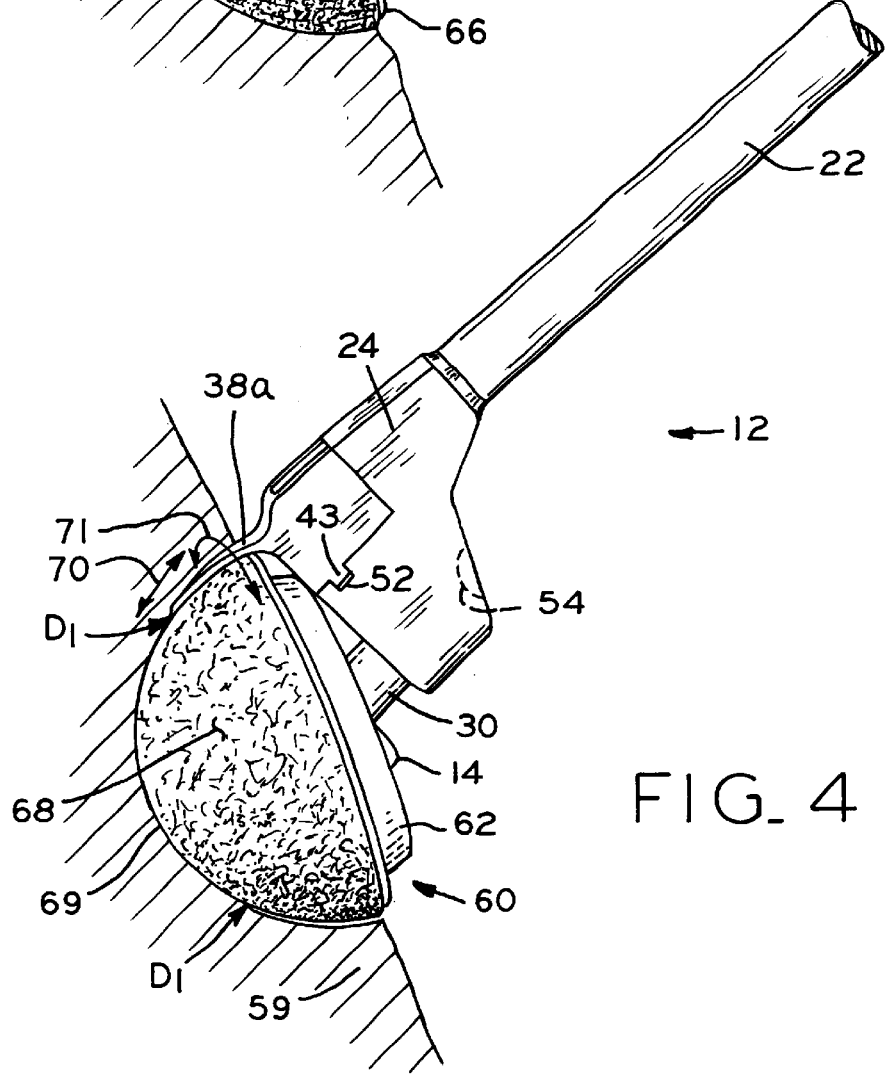
FIG. 4 is a partial sectional view showing the osteotome instrument of FIG. 3 in a pivoted position, the osteotome blade cutting bone adjacent the acetabulum to a first depth.

Handle shaft 22 of instrument 12 may be pivoted as shown in FIG. 4, such that blade 38a moves along the path of arrow 70, and end cutting surface 40 of blade 38a cuts bone 59 around outer hemispherical surface 68 of acetabular cup 60 in a direction from rim 66 toward apex 69 of acetabular cup 60. Thereafter, handle shaft 22 of instrument 12 may be pivoted in the reverse direction along the path of arrow 70 to withdraw blade 38a, wherein during such withdrawal, the engagement between tooth 43 of osteotome 16a within notch 52 in head 24 of instrument 12 prevents disengagement of osteotome 16a from instrument 12 in the event that blade clamping screw 50 is not sufficiently tightened. Impaction head 26 (FIGS. 1 and 2) may be struck with a mallet (not shown) as needed to drive blade 38a of osteotome 16a through bone 59 adjacent acetabulum 58.

Handle lever 27 (FIG. 2) of instrument 12 may be used to rotate instrument 12 such that blade 38a of osteotome 16a is moved to a position radially spaced from the first cut location, and handle shaft 22 may be pivoted to effect another cut from rim 66 toward apex 69 of acetabular cup 60. In this manner, several cuts may be made circumferentially about rim 66 of acetabular cup 60 to cut bone 59 away from acetabular cup 60 to a first depth $D_1$, which generally corresponds to the length of short blade 38a. Additionally, as shown by arrow 71 in FIG. 4, handle lever 27 of instrument 12 may be used to rotate blade 38a, striking handle lever 27 as necessary with a mallet (not shown), to make an orbital cut about the outer hemispherical surface 68 of acetabular cup 60 using side cutting surfaces 42 of blade 38a.

Advantageously, as may be seen in FIGS. 4 and 5, blade 38a is spaced closely adjacent outer hemispherical surface 68 of acetabular cup 60 during the cutting procedure described above, allowing bone 59 around acetabular cup 60 to be cut closely adjacent to acetabular cup 60, such that loss of bone 59 is minimized.

As shown in FIG. 5, a second osteotome 16b having long blade 38b may be attached to head 24 of instrument 12 as described above, wherein blade 38b extends to apex 69 of acetabular cup 60 when instrument 12 is pivoted along the direction of arrow 70. Instrument 12, with osteotome 16b attached thereto, is used in the same manner as described above to cut bone 59 surrounding acetabular cup 60 from first depth $D_1$ to a second depth $D_2$ at apex 69 of acetabular cup 60. After bone 59 surrounding acetabular cup 60 is cut away therefrom, acetabular cup 60 may be removed from acetabulum 61, leaving an intact, hemispherical recess in acetabulum 58 into which a replacement acetabular cup (not shown) may be easily fitted.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An apparatus for removing an acetabular cup from an acetabulum, said apparatus comprising:

a handle;

a pivot element connected to said handle, said pivot element dimensioned to be received within an acetabular cup; and a blade connected to said handle and spaced from said pivot element, such that when said pivot element is received within said acetabular cup, said blade is disposed externally of said acetabular cup closely adjacent an outer surface of said acetabular cup.

2. The apparatus of claim 1, wherein said pivot element is a spherical head, wherein at least a portion of said spherical head is spherically shaped.

3. The apparatus of claim 1, wherein the acetabular cup includes a hemispherical outer surface, and said blade is curved to conform to the outer surface.

4. The apparatus of claim 1, wherein said handle includes a head portion, and each of said pivot element and said blade are removably attached to said head portion.

5. The apparatus of claim 4, wherein said head portion includes a clamping member for securing one of said blade thereto.

6. The apparatus of claim 4, wherein said head portion includes one of a tooth and a notch and said blade includes the other of said tooth and said notch, said tooth and said notch engaging one another to prevent relative sliding movement between said head portion and said blade.

7. The apparatus of claim 1, wherein said handle includes a head portion disposed on a first end thereof to which said pivot element and said blade are removably attached, and a second end opposite said first end and including a shaft disposed substantially perpendicular to said handle.

8. A kit for removing an acetabular cup from an acetabulum, comprising:

an osteotome instrument;

a spherical head removably mountable to said instrument, said spherical head sized to be received within an acetabular cup; and a blade removably mountable to said instrument.

9. The kit of claim 8, wherein said blade is curved to conform to the outer surface of an acetabular cup having a hemispherical outer surface.

10. The kit of claim 8, including a plurality of said spherical heads of different sizes, said spherical heads respectively dimensioned to be received within acetabular cups of different sizes.

11. The kit of claim 8, including a plurality of said blades, said blades having respectively different lengths.

12. The kit of claim 8, wherein said instrument includes a handle and a head portion, said spherical head and said blade removably attached to said head portion.

13. The kit of claim 12, wherein said head portion includes one of a tooth and a notch and said blade includes the other of said tooth and said notch, said tooth and said notch engaging one another to prevent relative sliding movement between said head portion and said blade.

14. The kit of claim 8, wherein said instrument further includes a clamping member for securing one of said blades thereto, and said kit further includes a tool operable with said clamping member to secure said blade to said instrument and to release said blade from said instrument.

15. The kit of claim 8, wherein at least a portion of said spherical head is spherically shaped, said spherical head further including at least one indentation within said spherically shaped portion.

16. A method for removing an acetabular cup from an acetabulum, the acetabular cup having an outer surface, said method comprising the steps of:

providing an instrument including a spherical head and a blade, the spherical head and the blade spaced from one another;

seating the spherical head within the acetabular cup;

moving the instrument to make a series of cuts with the blade which are closely adjacent the outer surface of the acetabular cup; and removing the acetabular cup from the acetabulum.

17. The method of claim 16, further including, before said providing step, the additional steps of:

selecting a spherical head from a plurality of spherical heads of different sizes; and attaching the spherical head to the instrument.

18. The method of claim 17, further including, before said providing step, the additional steps of:

selecting a blade from a plurality of blades of different lengths; and attaching the blade to the instrument.

* * * * *